(12) United States Patent
Kondo et al.

(10) Patent No.: US 11,320,546 B2
(45) Date of Patent: May 3, 2022

(54) RADIATION IMAGING APPARATUS (71) Applicant: CANON KABUSHIKI KAISHA, Tokyo (JP)

(72) Inventors: Hiroto Kondo, Machida (JP); Masataka Suzuki, Yokohama (JP); Katsushi Kato, Kawasaki (JP); Shichihei Sakuragi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 12 days.

(21) Appl. No.: 16/929,815

(22) Filed: Jul. 15, 2020

(65) Prior Publication Data
US 2020/0348427 A1 Nov. 5, 2020

Related U.S. Application Data (63) Continuation of application No. PCT/CN2019/002683, filed on Jan. 28, 2019.

(30) Foreign Application Priority Data

Mar. 20, 2018 (JP) .............................. JP2018-052918

(51) Int. Cl.
*G01T 1/29* (2006.01)
*G01T 1/17* (2006.01)
*G01T 1/20* (2006.01)
*G01T 7/00* (2006.01)
*G08C 17/02* (2006.01)
*A61B 6/00* (2006.01)
*G03B 42/04* (2021.01)

(52) U.S. Cl.
CPC .............. *G01T 1/2992* (2013.01); *A61B 6/00* (2013.01); *G01T 1/17* (2013.01); *G01T 1/20188* (2020.05); *G01T 7/00* (2013.01); *G08C 17/02* (2013.01); *G01T 1/20* (2013.01); *G03B 42/04* (2013.01)

(58) Field of Classification Search
CPC .... A61B 6/00; G01T 1/17; G01T 1/20; G01T 1/20188; G01T 1/2992; G01T 7/00; G03B 42/04; G08C 17/02
See application file for complete search history.

(56) References Cited

U.S. PATENT DOCUMENTS

| 8,822,937 | B2 | 9/2014 | Koyanagi |
| 8,946,634 | B2 | 2/2015 | Watano |
| 9,668,707 | B2 | 6/2017 | Watanabe et al. |

(Continued)

FOREIGN PATENT DOCUMENTS

| JP | H07-280944 | 10/1995 |
| JP | 2004-252562 A | 9/2004 |

(Continued)

*Primary Examiner* — Mark R Gaworecki
(74) *Attorney, Agent, or Firm* — Venable LLP (57) ABSTRACT

A radiation imaging apparatus comprises a radiation detection unit configured to convert received radiation into an electrical signal, a communication unit configured to perform wireless communication with an external device, and an exterior at least partially formed by a non-conductive member and configured to contain the radiation detection unit and the communication unit, wherein a conductor is formed so as to cover the radiation detection unit, and the communication unit is arranged between the exterior and the conductor.

17 Claims, 6 Drawing Sheets

(56) References Cited

U.S. PATENT DOCUMENTS

| | | |
|---|---|---|
| 9,955,931 B2 | 5/2018 | Bettouyashiki et al. |
| 9,976,897 B2 | 5/2018 | Suzuki et al. |
| 10,024,980 B2 | 7/2018 | Suzuki et al. |
| 10,061,042 B2 | 8/2018 | Suzuki et al. |
| 10,067,250 B2 | 9/2018 | Kato et al. |
| 10,119,859 B2 | 11/2018 | Suzuki et al. |
| 10,139,722 B2 | 11/2018 | Ando |
| 10,156,641 B2 | 12/2018 | Hiratsuka et al. |
| 10,274,613 B2 | 4/2019 | Suzuki et al. |
| 10,648,854 B2 | 5/2020 | Suzuki et al. |
| 2007/0272873 A1 | 11/2007 | Jadrich |
| 2013/0099130 A1* | 4/2013 | Nakahashi ............. A61B 6/00 250/394 |
| 2013/0140467 A1 | 6/2013 | Kitano |
| 2013/0301803 A1 | 11/2013 | Liu |
| 2015/0305699 A1 | 10/2015 | Sakuragi et al. |
| 2016/0081639 A1 | 3/2016 | Bettouyashiki |
| 2016/0089092 A1* | 3/2016 | Shimizukawa ...... A61B 6/4233 378/98 |
| 2018/0321392 A1 | 11/2018 | Suzuki et al. |

FOREIGN PATENT DOCUMENTS

| | | |
|---|---|---|
| JP | 2010-276687 | 12/2010 |
| JP | 2011-058999 | 3/2011 |
| JP | 2011-112923 | 6/2011 |
| JP | 2012-112699 A | 6/2012 |
| JP | 2013-224949 A | 10/2013 |
| JP | 2013-250103 | 12/2013 |
| JP | 2014-25847 A | 2/2014 |
| JP | 5731505 B2 | 6/2015 |
| JP | 2016-27888 A | 2/2016 |
| JP | 2016-063874 | 4/2016 |
| JP | 2016-144582 | 8/2016 |
| JP | 2018-004520 | 1/2018 |
| WO | 2011/148960 A1 | 12/2011 |

* cited by examiner

RADIATION IMAGING APPARATUS

CROSS-REFERENCE TO RELATED APPLICATIONS

This application is a Continuation of International Patent Application No. PCT/JP2019/002683, filed Jan. 28, 2019, which claims the benefit of Japanese Patent Application No. 2018-052918, filed Mar. 20, 2018, both of which are hereby incorporated by reference herein in their entirety.

BACKGROUND OF THE INVENTION

Field of the Invention

The present invention relates to a radiation imaging apparatus that performs wireless communication with an external unit.

Background Art

A DR (Digital Radiography) apparatus, that is, a radiation imaging apparatus can be an expensive medical device since a semiconductor sensor is incorporated in the apparatus. Hence, to reduce the cost, the use of a resin as a housing material of the exterior of the radiation imaging apparatus is being considered. Although an inexpensive medical device can be implemented by using a resin as the housing material, noise may become a problem since a member that can shield the semiconductor sensor from external electromagnetic waves will not be present.

As a measure against noise caused by external electromagnetic waves in a radiation imaging apparatus using a resin as a housing material, PTL 1 discloses a radiation imaging apparatus in which a circuit board is covered by a conductive layer. In addition, PTL 2 discloses an X-ray image sensor in which a conductive member such as an aluminum foil or the like has been arranged on the internal surface of a container for storing components.

CITATION LIST

Patent Literature
PTL1 Japanese Patent Laid-Open No. 2010-276687
PTL2 Japanese Patent Laid-Open No. 7-280944

As described in PTL 1 and PTL 2, as a measure against noise caused by external electromagnetic waves of the radiation imaging apparatus, a semiconductor sensor that is to be incorporated is covered by a conductor. However, a communication unit for performing wireless communication tends to be incorporated in a radiation imaging apparatus that performs wireless communication. Since the radio waves emitted from the communication unit will be shielded if the periphery of the communication unit is covered by a conductor, it will become difficult to perform communication with an external unit.

To solve such a problem, the present invention provides a radiation imaging apparatus that can perform wireless communication with an external unit while shielding noise caused by electromagnetic waves.

SUMMARY OF THE INVENTION

According to one aspect of the present invention, there is provided a radiation imaging apparatus which comprises: a radiation detection unit configured to convert received radiation into an electrical signal; a communication unit configured to perform wireless communication with an external device; and an exterior at least partially formed by a non-conductive member and configured to contain the radiation detection unit and the communication unit, wherein a conductor is formed so as to cover the radiation detection unit, and the communication unit is arranged between the exterior and the conductor.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

The present invention will be described in detail hereinafter based on embodiments thereof with reference to the accompanying drawings. Note that arrangements to be shown in the embodiments below are merely examples, and the present invention is not limited to the arrangements to be illustrated.

(Arrangement of General Radiation Imaging Apparatus)

Figure 1A:
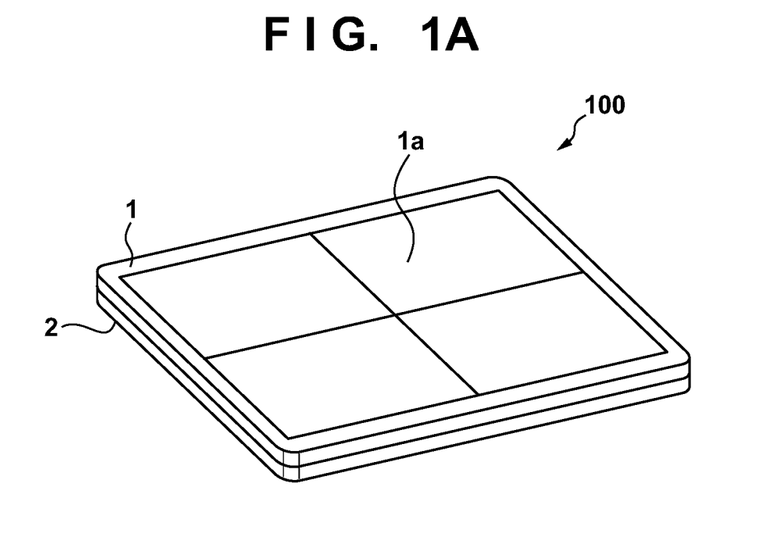
FIG. 1A is a view showing the main arrangement of a general radiation imaging apparatus.
Figure 1B:
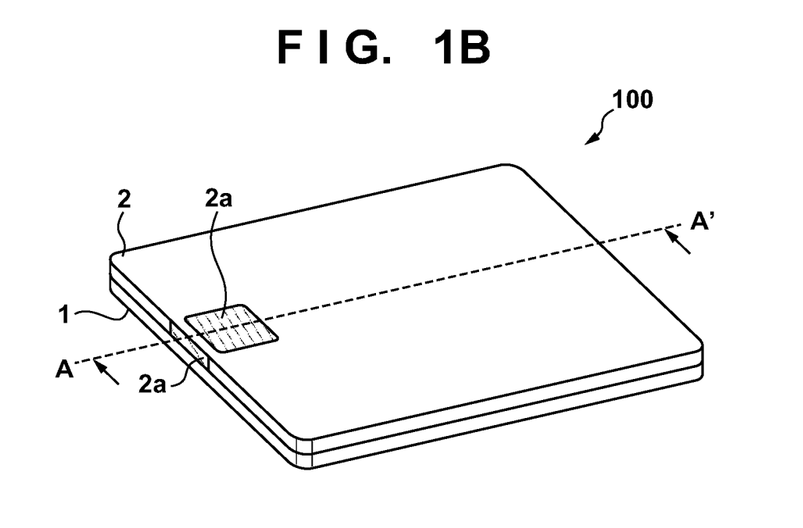
FIG. 1B is a view showing the main arrangement of the general radiation imaging apparatus.

The arrangement of a general radiation imaging apparatus will be described before the arrangement of a radiation imaging apparatus according to an embodiment of the present invention is described. FIGS. 1A and 1B are views showing the main arrangement of an imaging apparatus 100 which is a general radiation imaging apparatus (to be referred to as an imaging apparatus hereinafter). FIG. 1A shows a view seen from the side of the front surface of the imaging apparatus 100, and FIG. 1B shows a view seen from the side of the back surface of the imaging apparatus 100. The exterior of the imaging apparatus 100 is formed by a front housing 1 which includes a radiation reception surface 1a and a rear housing 2 which includes a radio transmission window 2a for allowing wireless communication. Assume that the exterior of the imaging apparatus 100, that is, the material of the front housing 1 and the rear housing 2 is a high-strength lightweight material such as CFRP, an aluminum alloy, a magnesium alloy, or the like. A material with good radiation transmittance needs to be selected for the radiation reception surface 1a of the front housing 1. Hence, when a metallic material such as an aluminum alloy, a magnesium alloy, or the like is to be used as the material of the exterior, the radiation reception surface 1a can be set as the opening, and a component that has high radiation transmittance and high rigidity such as CFRP or the like can be formed on the radiation reception surface 1a.

Figure 2:
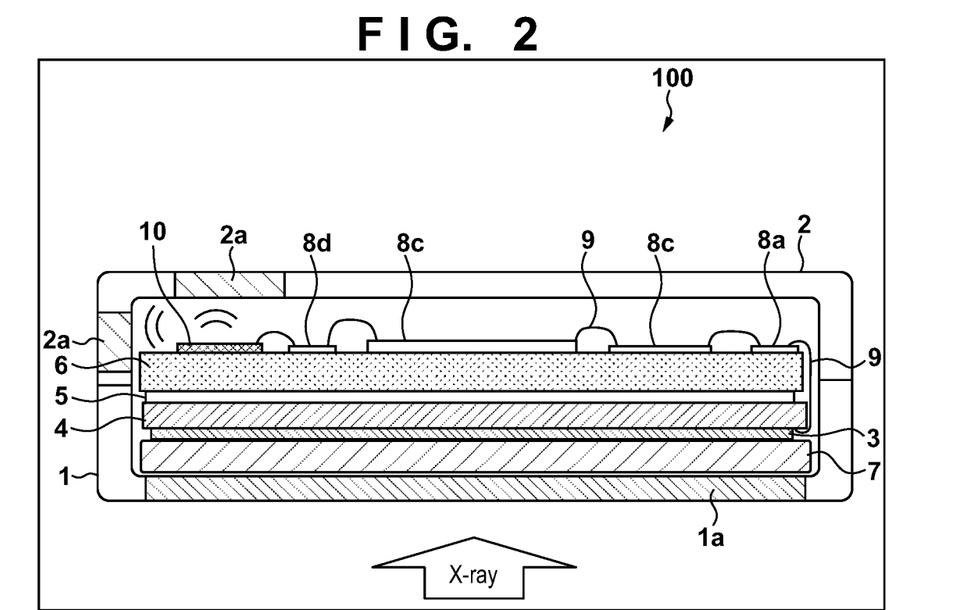
FIG. 2 is a sectional view taken along a line A-A' in FIG. 1B.

FIG. 2 shows a sectional view taken along a line A-A' in FIG. 1B. A fluorescent material 3 that receives the radiation transmitted through an object and converts the received radiation into light is stacked on a sensor 4 which serves as a radiation detection unit. The converted light is converted into an electrical signal by the sensor 4. The sensor 4 is attached to a sensor holding member 6 via a radiation shielding material 5. In general, GOS ($Gd_2O_2S$) or CsI is used as the material of the fluorescent material 3 to be stacked on the sensor 4. In general, since the sensor 4 is made of glass, the sensor will break if it receives a strong impact, load or displacement. Hence, an impact absorbing member 7 for absorbing an impact is arranged on the side of the radiation reception surface of the sensor 4. A material which has high radiation transmittance needs to be selected as the impact absorbing member 7 so as to allow the radiation transmitted through the object to reach the fluorescent material 3 without attenuation as much as possible. The radiation shielding material 5 has a function of protecting the electrical circuit boards from the radiation transmitted through the object and the sensor 4 and a function of preventing the radiation transmitted through the imaging apparatus 100 and scattered by a wall or the like behind the imaging apparatus from bouncing back and re-entering the fluorescent material 3 and the sensor 4. Hence, Mo, W, Pb, Al, Cu, SUS, barium sulfate, or the like tends to be employed as the material of the radiation shielding material.

Electrical circuit boards 8a and 8b for reading out the electrical signals converted by the sensor 4 via a cable 9, an electrical circuit board 8c for generating a radiation image (image data) after the readout, and a communication module board 8d are installed on a surface facing a sensor attachment surface of the sensor holding member 6. The generated radiation image is transmitted to an external device (not shown) such as a PC, a tablet, or the like, and can be displayed to an operator or the like. Although the communication method may be wired communication or wireless communication, assume that the imaging apparatus 100 performs at least a wireless communication operation and includes a wireless communication unit 10. The wireless communication unit 10 performs communication on, for example, the 2.4 GHz band or the 5 GHz band. The radio transmission window 2a is arranged since the wireless radio waves will be shielded in a case in which the exterior of the imaging apparatus is made of a metallic material, and the wireless communication unit 10 is arranged at a position close to the radio transmission window 2a in consideration of the wireless radiation characteristics.

Figure 3:
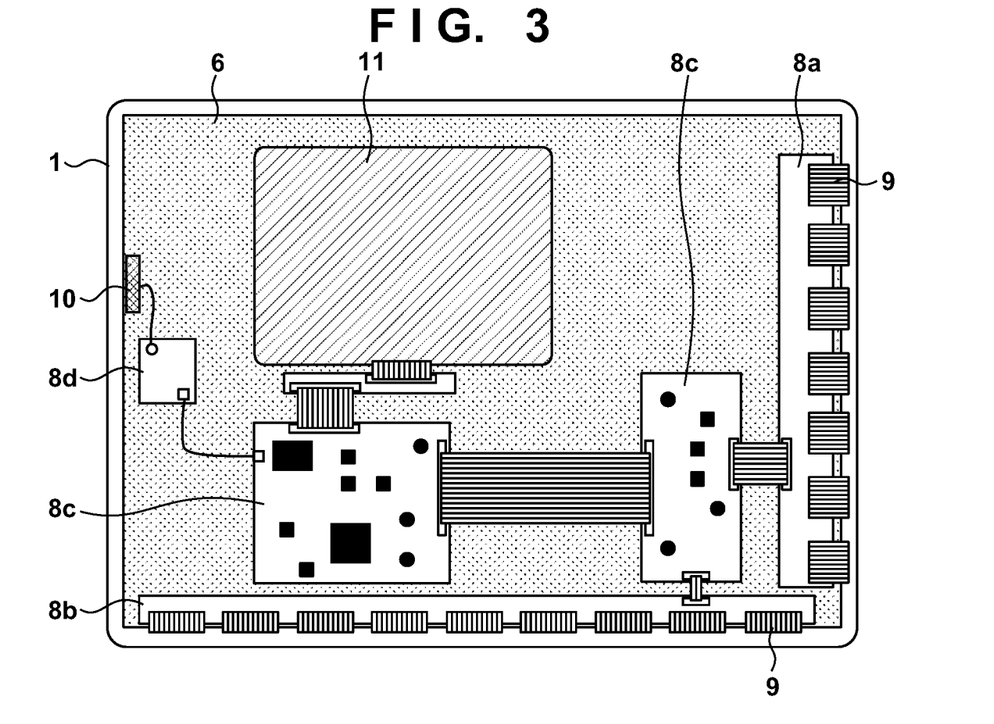
FIG. 3 is a view of an imaging apparatus 100 in which a rear housing 2 has been removed.

FIG. 3 is a view of the arrangement of the imaging apparatus 100 in a case in which the rear housing 2 has been removed. Since the imaging apparatus 100 operates wirelessly, a power supply 11 for driving the imaging apparatus 100 has been included. In general, a secondary battery such as a lithium-ion battery, a lithium-ion capacitor, or the like tends to be employed as the power supply 11 to allow charging, but the arrangement is not limited to this. Also, although the power supply 11 is arranged to be incorporated in the imaging apparatus 100 in FIG. 3, it may also be arranged to have a structure that considers the ease of detachability, and the power supply is not limited to an incorporated arrangement. A structure in which the power supply 11 is easily detachable may be, for example, a structure in which the power supply 11 can be directly accessed without requiring the removal of the rear housing 2.

First Embodiment

Figure 4:
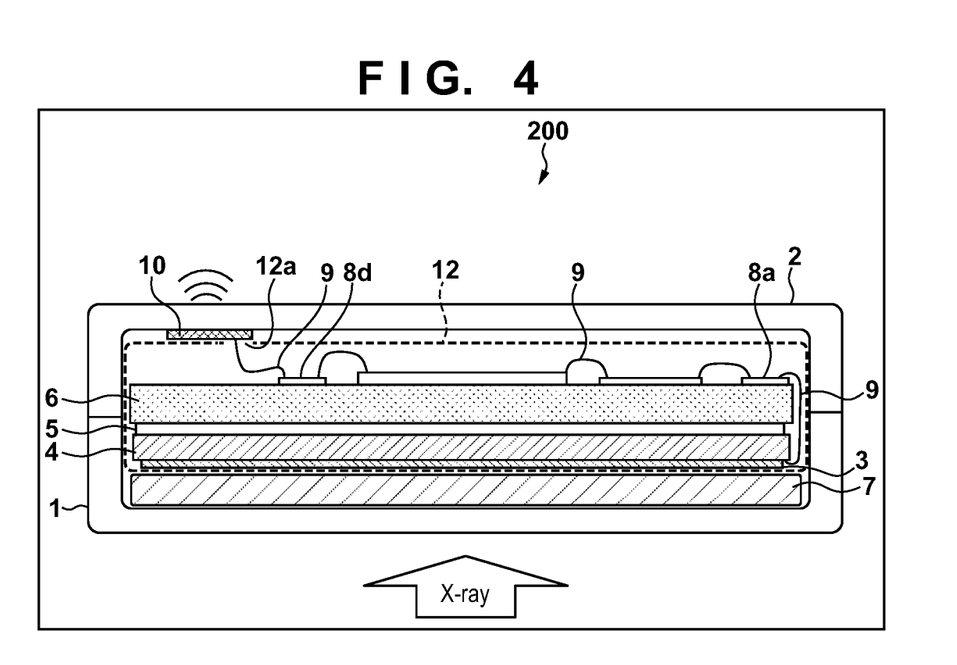
FIG. 4 is a sectional view of a radiation imaging apparatus according to the first embodiment.

The arrangement of an imaging apparatus according to the first embodiment will be described next. FIG. 4 shows a sectional view of an imaging apparatus 200 according to this embodiment. Both of a front housing 1 and a rear housing 2, which are the exterior of the imaging apparatus 200, are formed by a non-metallic material (non-conductive member). Since a non-metallic material is used for the exterior, the electromagnetic shielding capability of the exterior will be very low, and the exterior will not become an obstacle for performing wireless communication. However, using a material with low electromagnetic shielding capability can greatly increase the possibility of artifact generation due to the application of electromagnetic waves to a sensor 4, electrical circuit boards 8a to 8c, a communication module board 8d, and a cable 9.

As a measure against this artifact generation, the imaging apparatus 200 has a structure in which the above-described artifact generation is suppressed by covering the components inside the imaging apparatus 200 by a conductor 12. The conductor 12 suffices to be a conductor, and the material and the shape of the conductor 12 are not limited as long as a conductive film material, a sheet metal material, or the like is employed. However, as described above, the wireless radio waves will be shielded if a wireless communication unit 10 is covered by the conductor 12. Hence, as shown in FIG. 4, the wireless communication unit 10 can be arranged between the conductor 12 and the exterior of the imaging apparatus 200 to allow radiation imaging to be performed without an obstacle to the wireless communication while taking a measure against electromagnetic noise. Furthermore, since the material of the exterior is a non-metallic material, the entire exterior can become a wireless radio transmission window, thus increasing stability in the communication with an external communication unit. On the other hand, since the wireless communication unit 10 and the communication module board 8d are connected by the cable 9, the conductor 12 has an opening 12a only for the cable 9 to pass through. Since the opening 12a is used for the purpose of passing the cable 9, it is preferable, from the point of view of electromagnetic shielding, for the opening 12a to have the smallest opening size as possible for the cable 9 to pass through. Note that although the wireless communication unit 10 is arranged on the back-surface side (the inner surface of the wall facing a radiation reception surface 1a) of the imaging apparatus 100 in FIG. 4, it suffices to be arranged at a position which will not overlap the effective pixel region of the radiation reception surface 1a, and may be arranged on an adjacent side surface (the inner surface of an adjacent side wall of the radiation reception surface 1a). Also, although the impact absorbing member 7 is arranged on the outside of the conductor 12 in a manner similar to the wireless communication unit 10, the impact absorbing member may also be covered by the conductor 12 in a manner similar to the sensor 4 and the like.

In this manner, in the imaging apparatus 200 according to this embodiment, the components inside the imaging apparatus 200 are covered by the conductor 12 to reduce the influence of electromagnetic waves from the wireless communication unit 10 on the internal components. As a result, the possibility that an artifact will be generated on a radiation image obtained by radiation imaging will be reduced.

Second Embodiment

Figure 5:
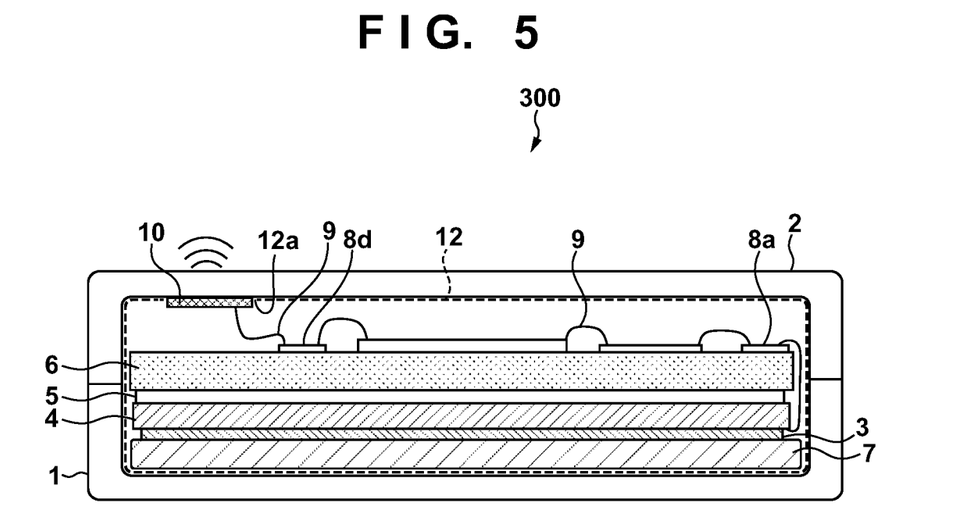
FIG. 5 is a sectional view of a radiation imaging apparatus according to the second embodiment.

The arrangement of an imaging apparatus according to the second embodiment will be described next. Only points different from the first embodiment will be described hereinafter. FIG. 5 is a sectional view of an imaging apparatus 300 according to this embodiment. In the imaging apparatus 300, conductors 12 are formed along an inner wall (inner surface) of a front housing 1 and an inner wall (inner surface) of a rear housing 2, respectively. Each conductor 12 may be a conductive film material or a sheet metal material in similar manner to the first embodiment or may be a conductive coating (conductive coating film) or a conductive plating. In a case in which a conductive coating or plating is to be employed as the conductor 12, communication with an external device can be performed without a problem by, for example, masking only the portion where a wireless communication unit 10 is to be arranged and arranging the wireless communication unit 10 at a location where an opening 12a has been formed. Also, in a case in which the conductor 12 is to be made of a conductive film material, a sheet metal material, or the like, it will be possible to perform communication with an external device without a problem in a similar manner to the above-described arrangement by forming the opening 12a in only a portion where the wireless communication unit 10 is to be arranged.

Figure 6:
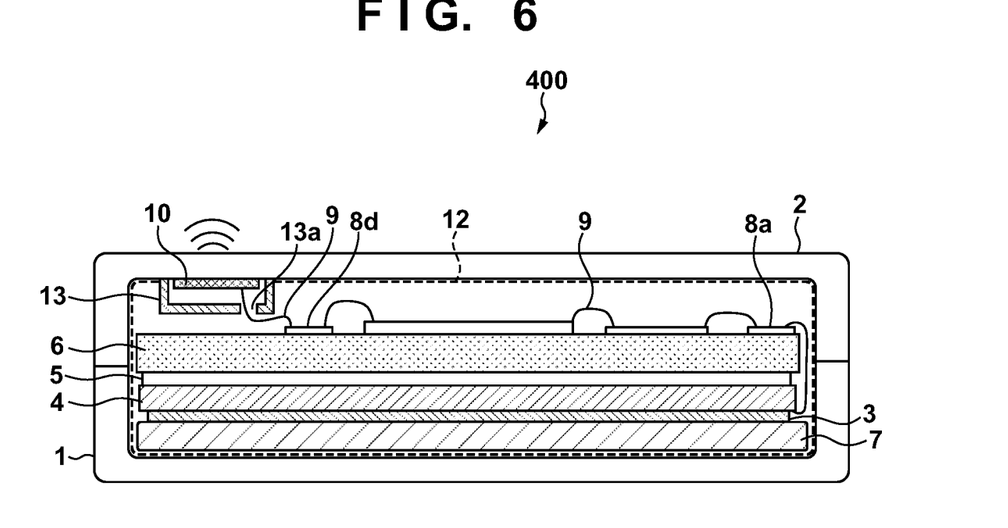
FIG. 6 is a sectional view of the radiation imaging apparatus according to the second embodiment.

FIG. 6 shows an imaging apparatus 400 as a modification of this embodiment. In the imaging apparatus 400, a conductive member 13 is formed so as to surround the wireless communication unit 10 to prevent the electromagnetic waves from the wireless communication unit 10 from entering inside the imaging apparatus 400. The conductive member 13 is electrically connected to the conductor 12. In this arrangement, an opening 13a can be arranged in the conductive member 13 to allow the wireless communication unit 10 to be connected to a communication module board 8d. In addition, in this arrangement, since the opening 13a is an opening for a cable 9 to pass through, it is preferable for the opening 13a to have the smallest opening size for the cable 9 to pass through.

Figure 7:
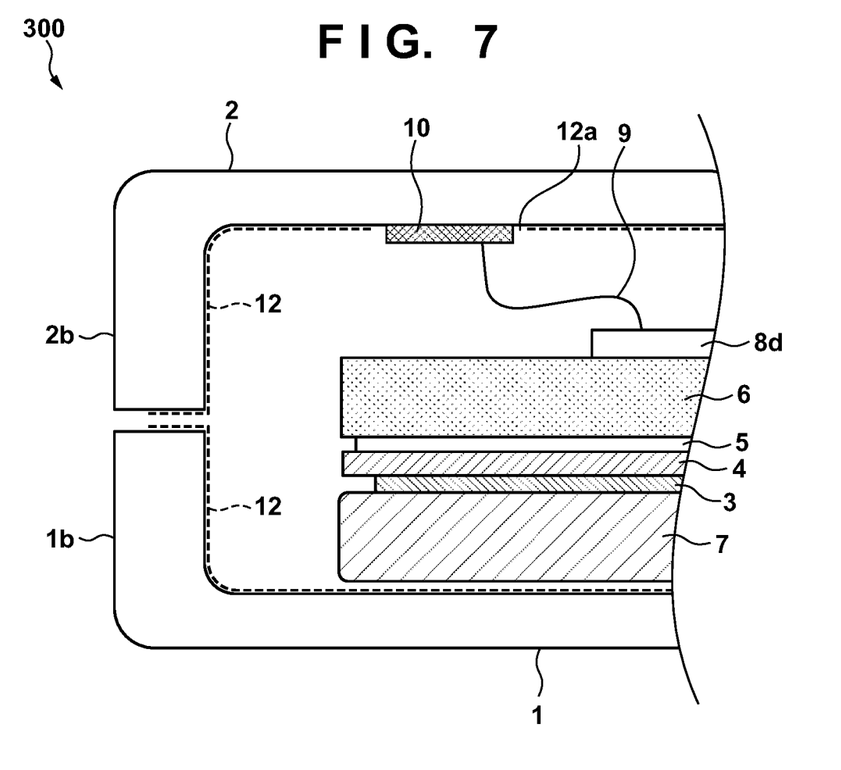
FIG. 7 is an enlarged view of a portion joining a front housing and a rear housing of the radiation imaging apparatus according to the second embodiment.

In both the imaging apparatus 300 shown in FIG. 5 and the imaging apparatus 400 shown in FIG. 6, the conductors 12 are formed along the inner wall of the front housing 1 and the inner wall of the rear housing 2, respectively. In this case, the electromagnetic waves can be more effectively prevented from entering a sensor 4, electrical circuit boards 8a to 8c, and the like by forming the conductors 12 so as to be electrically connected in series. FIG. 7 shows an enlarged view of a portion joining the front housing and the rear housing in a case in which the conductors 12 have been formed so as to be electrically connected in series in the imaging apparatus 300 (FIG. 5). As shown in FIG. 7, the conductors 12, arranged on the side of the front housing 1 and the side of the rear housing 2, respectively, can be formed extending to the joint portions of the respective housings so that the conductors will overlap when the housings are joined. As a result, the conductors 12 will come into contact and become electrically connected when the imaging apparatus 300 is assembled. Also, in a case in which the conductors 12 are to be formed by the respective housings, it is preferable to form the conductors up to the positions that will not reach a side surface 1b of the front housing and a side surface 2b of the rear housing (that is, the outer walls), respectively, as shown in FIG. 7 in consideration of the entry of static electricity or the like from the outside.

In this manner, in the imaging apparatus 300 according to this embodiment, the components in the imaging apparatus 300 are covered by the conductors 12 formed along the inner sides of the respective housings. Furthermore, in the imaging apparatus 400 according to the modification, the wireless communication unit 10 is covered by the conductive member 13. Hence, the influence of electromagnetic waves from the wireless communication unit 10 on the internal components can be reduced. As a result, the possibility that an artifact will be generated on a radiation image obtained by radiation imaging will be reduced.

Third Embodiment

Figure 8:
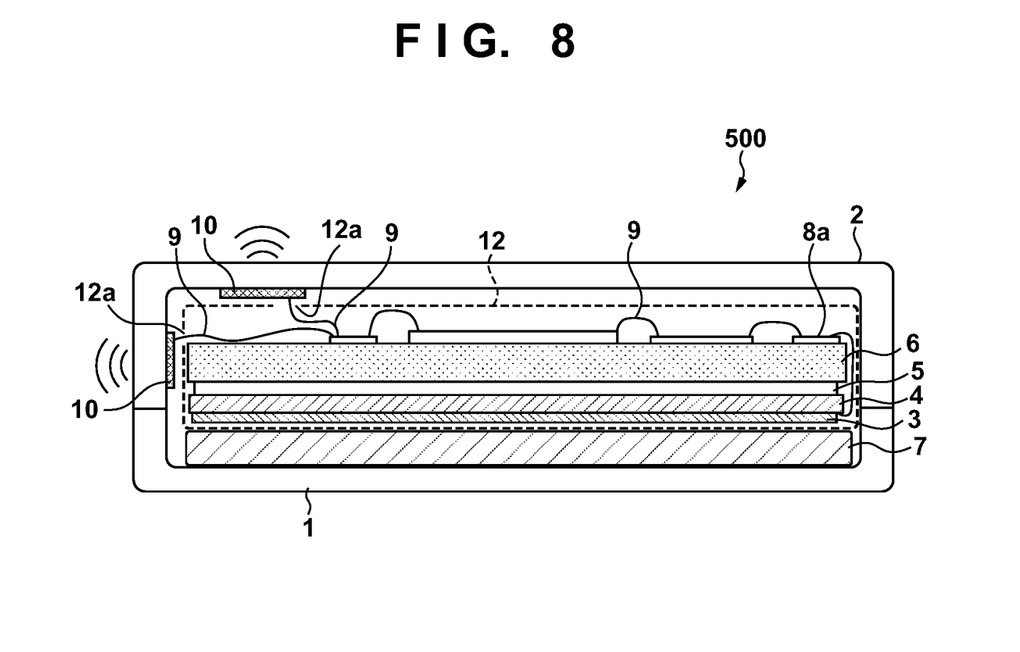
FIG. 8 is a sectional view of a radiation imaging apparatus according to a third embodiment.

The arrangement of an imaging apparatus according to the third embodiment will be described next. Only points different from the above-described embodiments will be described hereinafter. FIG. 8 shows a sectional view of an imaging apparatus 500 according to this embodiment. A plurality of wireless communication units 10 have been arranged in the imaging apparatus 500 in consideration of communication stability in wireless communication. A radiation imaging apparatus can be installed in various kinds of places such as behind or underneath a patient, inside a bed, and the like when an imaging operation is to be performed. To transfer a radiation image to an external device immediately after an imaging operation, it is important for the radiation imaging apparatus to have a structure in which the wireless radio waves can be transmitted in all directions without any obstacles. Hence, as shown in FIG. 8, the plurality of wireless communication units 10 have been arranged on at least one set of adjacent surfaces in the imaging apparatus 500. In FIG. 8, the imaging apparatus has a structure similar to that shown in FIG. 4 according to the first embodiment in that a sensor 4 and the like are covered by a conductor 12 and each wireless communication unit 10 is installed between the conductor 12 and a rear housing 2. Note that the arrangement of the plurality of the wireless communication units 10 is not limited to that shown in FIG. 8, and it may be arranged so that the plurality of the wireless communication units 10 are arranged on the same plane.

Figure 9:
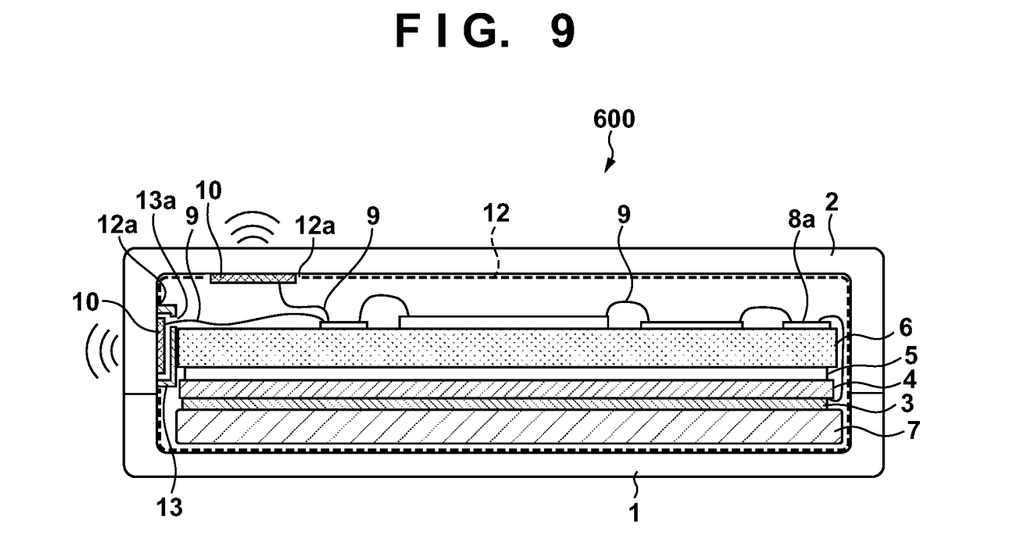
FIG. 9 is a sectional view of the radiation imaging apparatus according to the third embodiment.

FIG. 9 shows an imaging apparatus 600 according to a modification of this embodiment. In the imaging apparatus 600, the conductor 12 is formed along the inner walls (inner surfaces) of a front housing 1 and the rear housing 2. Although openings 12a for allowing communication by the respective wireless communication units 10 have been arranged, a conductive member 13 has been installed in the periphery of the wireless communication unit 10 which is arranged on the side surface. In a case in which a radiation shielding material 5 is made of a metallic material, a state in which the electromagnetic waves that enter from the opening 12a on the side of the back surface are absorbed by the radiation shielding material 5 before the electromagnetic waves reach the sensor 4 can be considered. In contrast, the opening 12a on the side of the side surface is adjacent to the sensor 4, and there is nothing between the opening 12a on the side of the side surface and the sensor 4 to shield the electromagnetic waves. Hence, the conductive member 13 is arranged at the opening 12a of the side surface. In this case, it is preferable to arrange an opening 13a, which is to be provided in the conductive member 13, at a position far from the sensor 4, that is, a position closer to the side of the back surface than the radiation shielding material 5.

In this manner, in the imaging apparatus 500 according to this embodiment, although the plurality of wireless communication units 10 are included to improve the communication stability, the influence of the electromagnetic waves from the wireless communication units 10 on the internal components is reduced by covering the internal components by the conductor 12. Furthermore, in the imaging apparatus 600 as a modification, the conductor 12 and the conductive member 13 are formed in accordance with the state of the periphery of the position of each of the plurality of wireless communication units 10 to effectively reduce the influence of the electromagnetic waves from the wireless communication units 10 on the internal components. As a result, the possibility that an artifact will be generated on a radiation image obtained by radiation imaging will be reduced.

Fourth Embodiment

Figure 10:
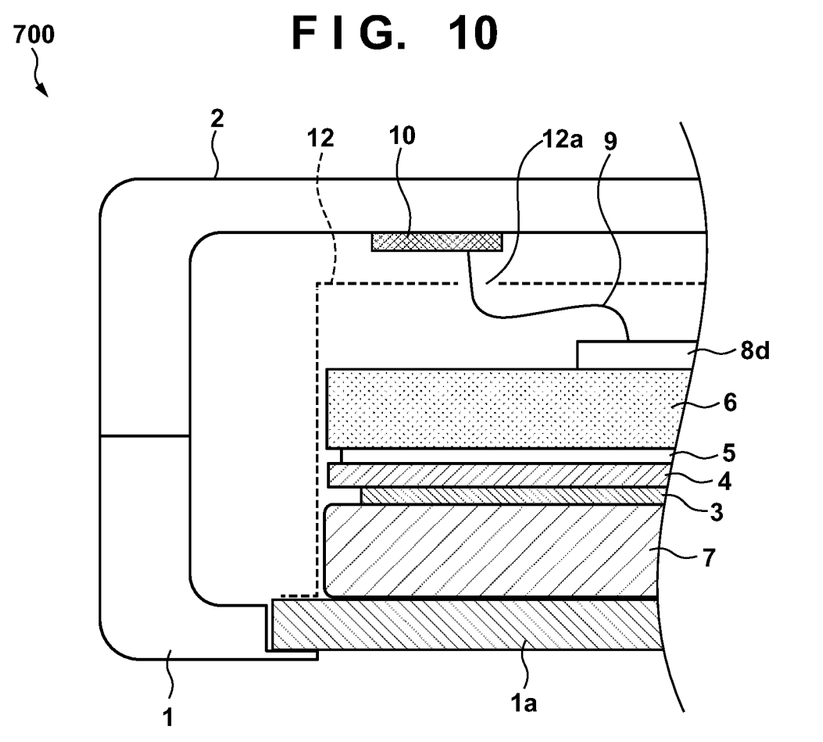
FIG. 10 is a partially enlarged view of a section of a radiation imaging apparatus according to the fourth embodiment.

The arrangement of an imaging apparatus according to the fourth embodiment will be described next. On points different from the above-described embodiments will be described hereinafter. FIG. 10 shows a sectional view of an imaging apparatus 700 according to this embodiment. The imaging apparatus 700 has a structure in which a front housing 1 is a separate component from a radiation reception surface 1a and the radiation reception surface 1a is a conductive member. A conductor 12 covers internal components other than a wireless communication unit 10 in the imaging apparatus 700, and each end of the conductor 12 is connected to the radiation reception surface 1a. In this case, the conductor 12 and the radiation reception surface 1a can be stably electrically connected by employing a method such as adhesion by a conductive adhesive or a conductive tape, fitting, or the like. In addition, in a structure in which the conductor 12 is arranged along the inner wall of the front housing 1 and the inner wall of a rear housing 2, the conductor 12 and the radiation reception surface 1a can be electrically connected at the contact point of the front housing 1 and the radiation reception surface 1a shown in FIG. 10.

In this manner, in the imaging apparatus 700 according to this embodiment, even in a case in which a part of the exterior is a conductive member, the same effect as that in the above-described embodiments can be obtained by arranging the conductor 12.

Other Embodiments

The property of a conductor 12 according to the embodiments described above can be changed in accordance with the position at which the conductor 12 is to be formed. For example, the material quality, the thickness, the thermal conductivity, the radiation transmittance, the volume resistivity of the conductor 12, and the like may be changed between the side of the radiation reception surface and the side on the back surface of the imaging apparatus. Regarding the thickness, if the thickness is increased, the thermal conductivity and the radiation transmittance will improve, and the electromagnetic waves can be shielded easily. Hence, by increasing the thickness of the conductor on the side of the back surface of the imaging apparatus, the heat dissipation from each electrical circuit board can be dispersed, and it will be possible to further prevent the backscattering of radiation. As a result, artifact generation on the radiation image can be suppressed. The property of the conductor 12 can be controlled easily when the imaging apparatus has a structure in which the conductor 12 is divided between the side of a front housing 1 and the side of a rear housing 2 in the manner of an imaging apparatus 300 shown in FIG. 7.

In addition, although each of the above-described embodiments has described an example in which a wireless communication unit 10 functions as a communication unit that transfers a radiation image to an external device, the wireless communication unit 10 may also function as a non-contact power supplying unit to a power supply 11. One of the plurality of wireless communication units 10 shown in FIGS. 8 and 9 may function as a power supplying unit in consideration of such an arrangement. In this case, from the point of view of the operation, the wireless communication unit 10 that is to function as the power supplying unit may be arranged on a side surface (an inner surface of an adjacent side wall of the radiation reception surface). This is because, as described in the first embodiment, the imaging apparatus is to be installed behind or underneath a patient or inside a bed, and arranging the wireless communication unit 10 that is to function as the power supplying unit on the side surface will make it easier for a corresponding power transmission unit (not shown) to connect when the power supply capacity of the power supply 11 has decreased during an imaging operation. Note that the arrangement of the wireless communication unit 10 that is to function as a power supplying unit is not limited to this arrangement.

According to the present invention, a radiation imaging apparatus that can perform wireless communication with an external unit while shielding noise caused by electromagnetic waves can be provided.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a radiation detection unit configured to convert received radiation into an electrical signal;
a communication unit configured to perform wireless communication with an external device; and
an exterior at least partially formed by a non-conductive member and configured to contain the radiation detection unit and the communication unit, wherein
a conductor is arranged so as to cover the radiation detection unit and an electrical board arranged behind the radiation detection unit, and
the communication unit is arranged between the exterior and the conductor.

2. The radiation imaging apparatus according to claim 1, wherein the conductor has a different property depending on a position.

3. The radiation imaging apparatus according to claim 1, wherein the communication unit includes a plurality of communication units which are to be arranged.

4. A radiation imaging apparatus, comprising:
a radiation detection unit configured to convert received radiation into an electrical signal;
a communication unit configured to perform wireless communication with an external device; and
an exterior at least partially formed by a non-conductive member and configured to contain the radiation detection unit and the communication unit, wherein
a conductor is formed so as to cover the radiation detection unit,
the communication unit is arranged between the exterior and the conductor, and
the conductor has an opening for passing a cable that connects the communication unit to the radiation detection unit.

5. A radiation imaging apparatus, comprising:
a radiation detection unit configured to convert received radiation into an electrical signal;
a communication unit configured to perform wireless communication with an external device;
an exterior at least partially formed by a non-conductive member and configured to contain the radiation detection unit and the communication unit, and
a conductive member formed so as to surround the communication unit, wherein
a conductor is formed so as to cover the radiation detection unit,
the communication unit is arranged between the exterior and the conductor,
at least a part of the conductor is one of a conductive film material and a sheet metal material, and
the conductive member has an opening for passing a cable that connects the communication unit to the radiation detection unit.

6. A radiation imaging apparatus, comprising:
a radiation detection unit configured to convert received radiation into an electrical signal;
a communication unit configured to perform wireless communication with an external device; and
an exterior at least partially formed by a non-conductive member and configured to contain the radiation detection unit and the communication unit, wherein
a conductor is formed so as to cover the radiation detection unit,
the communication unit is arranged between the exterior and the conductor,
a part of the exterior is a radiation reception surface, the communication unit is arranged on one of an inner surface of a side wall adjacent to the radiation reception surface and an inner surface of a wall facing the radiation reception surface, and
when the radiation reception surface is formed by a conductive member, the conductor is formed to be electrically connected to the radiation reception surface.

7. A radiation imaging apparatus, further, comprising:
a radiation detection unit configured to convert received radiation into an electrical signal;
a communication unit configured to perform wireless communication with an external device;
an exterior at least partially formed by a non-conductive member and configured to contain the radiation detection unit and the communication unit;
a power supply configured to drive the radiation imaging apparatus; and
a non-contact power supplying unit configured to supply a power to the power supply in a non-contact manner, wherein
a conductor is formed so as to cover the radiation detection unit, and
the communication unit and the non-contact power supplying unit are arranged between the exterior and the conductor.

8. A radiation imaging apparatus, comprising:
a radiation detection unit configured to convert received radiation into an electrical signal;
a communication unit configured to perform wireless communication with an external device; and
an exterior at least partially formed by a non-conductive member and configured to contain the radiation detection unit and the communication unit, wherein
a conductor is formed along an inner surface of the exterior, and
the communication unit is arranged in an opening provided in the conductor.

9. The radiation imaging apparatus according to claim 8, wherein the exterior is formed by assembling a first housing and a second housing, and
the conductor is formed so as to overlap when the first housing and the second housing are joined.

10. The radiation imaging apparatus according to claim 9, further comprising a conductive member formed so as to surround the communication unit.

11. The radiation imaging apparatus according to claim 10, wherein the conductive member has an opening for passing a cable that connects the communication unit to the radiation detection unit.

12. The radiation imaging apparatus according to claim 8, wherein at least a part of the conductor is selected from the group consisting of a conductive coating film, plating, a conductive film material, and a metal sheet material applied to the inner surface of the exterior.

13. The radiation imaging apparatus according to claim 8, wherein a part of the exterior is a radiation reception surface, and
the communication unit is arranged on one of an inner surface of a side wall adjacent to the radiation reception surface and an inner surface of a wall facing the radiation reception surface.

14. The radiation imaging apparatus according to claim 13, wherein when the radiation reception surface is formed by a conductive member, the conductor is formed to be electrically connected to the radiation reception surface.

15. The radiation imaging apparatus according to claim 8, wherein the conductor has a different property depending on a position.

16. The radiation imaging apparatus according to claim 8, wherein the communication unit includes a plurality of communication units that are to be arranged.

17. The radiation imaging apparatus according to claim 16, further comprising a power supply configured to drive the radiation imaging apparatus, wherein at least one of the plurality of communication units functions as a non-contact power supplying unit to the power supply.

* * * * *